United States Patent [19]

Van Aken

[11] 4,403,040

[45] Sep. 6, 1983

[54] DIAGNOSTIC TEST FOR THE DETECTION OF A SPECIFIC TUMOR ANTIGEN WITH COA-SPC

[76] Inventor: Morgan D. Van Aken, 8771 B Gilman Dr., La Jolla, Calif. 92037

[21] Appl. No.: 350,801

[22] Filed: Feb. 25, 1982

[51] Int. Cl.$^3$ .................... G01N 33/50; G01N 33/68
[52] U.S. Cl. .................................. 436/501; 436/64
[58] Field of Search ............. 23/230 B; 436/64, 501

[56] References Cited

U.S. PATENT DOCUMENTS

| | | | |
|---|---|---|---|
| 3,426,123 | 2/1969 | Hoff | 424/12 |
| 4,130,634 | 12/1978 | Molinaro | 23/230 B X |
| 4,160,817 | 7/1979 | Bucovaz | 260/112 B X |
| 4,261,967 | 4/1981 | Bucovaz | 436/64 |
| 4,284,552 | 8/1981 | Bucovaz | 260/112 R |
| 4,332,788 | 6/1982 | Mochida | 23/230 B X |
| 4,335,096 | 6/1982 | Tsuji | 23/230 B X |

OTHER PUBLICATIONS

E. T. Bucovaz et al., IRCS, Medical Science: Biochemistry: Biomedical Technology: Cancer: Clinical Biochemistry, 7, 71 (1979).

S. J. Tarnowski et al., Preparative Biochemistry, 10(3), 331, 336–341, (1980).

S. J. Tarnowski et al., Life Sciences, vol. 23, p. 2757, (1978).

E. T. Bucovaz et al., Third International Symp., Detection and Prevention of Cancer, vol. 3, pp. 258, 259, (1978).

Chemical Abstracts I, 86:69778c, (1977).
Chemical Abstracts II, 89:19771m, (1978).
Chemical Abstracts III, 89:103278p, (1978).
Chemical Abstracts IV, 92:176878f, (1980).

*Primary Examiner*—Sidney Marantz
*Attorney, Agent, or Firm*—Brown & Martin

[57] ABSTRACT

Diagnostic test method and composition for detection of tumor antigen indicating the possible presence of a carcinoma through agglutination association between tumor antigen in human sera and coenzyme A-synthesizing protein complex of bakers' yeast bonded to animal or human erythrocytes or to latex particles.

14 Claims, No Drawings

DIAGNOSTIC TEST FOR THE DETECTION OF A SPECIFIC TUMOR ANTIGEN WITH COA-SPC

FIELD OF THE INVENTION

This invention relates to an improved test method and composition for the diagnosis of many types of cancer and to an improved method for the therapeutic monitoring of various cancers or carcinomas.

BACKGROUND OF THE INVENTION

Cancer has always been a dreaded disease and with increasing concentration of carcinogens, it is a matter of increasing concern to all. Early detection and treatment are the best hope for curing or retarding cancer and the need for a test enabling early detection is great.

Detection procedures prior to the present invention have been uncertain, e.g. palpation, and/or complicated and expensive, e.g. fluoroscopy.

Researchers have been able to identify specific proteins and lipids in human sera that indicate the presence or carcinomas. These macromolecules are usually referred to as tumor antigens or tumor markers and have been demonstrated to be present in most carcinomas.

It has recently been found that a material known as coenzyme A-synthesizing protein complex, hereinafter referred to as CoA-SPC, of bakers' yeast, bonds to protein tumor antigen. The material has been labelled with a radioactive isotope and used in an R.I.A. method for detecting the presence or protein tumor antigen. However, the procedure is time consuming and the equipment for assay by this method is expensive. Also, decay of the radioactivity in the reagent and disposal of radioactive test material create problems, and possible transfer of radioactivity may interfere with the reliability of the test.

BRIEF STATEMENT OF THE INVENTION

It is an object of the present invention to provide a simple, accurate and rapid diagnostic test method for detection of carcinoma and a composition for use in that method for agglutination assay of tumor antigens in human sera. The novel composition is an aqueous suspension of CoA-SPC bonded to animal or human erythrocytes or to certain latex particles which is effective in the present method to associate with and agglutinate any tumor antigen in human sera to indicate the possible presence of a carcinoma.

DETAILED DISCLOSURE OF THE INVENTION

The cancer detecting composition of the present invention is an aqueous suspension of CoA-SPC secured to erythrocytes or to a latex particle effective when added to a measured quantity or serum accurately to determine the presence in that serum of protein tumor antigen with a minimum of false positive indications. The CoA-SPC material is a product derived from bakers' yeast according to procedures known per se. See an article by Tarnowski et al, entitled "Alternate Procedure for the Preparation of the coenzyme A-synthesizing Protein Complex of Bakers' Yeast" in *Preparative Biochemistry*, 10(3), 331–345 (1980). Briefly, the preparation involves dehydrating yeast of 37 degrees C to remove at least 66% of the original water by weight, preferably grinding the dried yeast and rehydrating the yeast to its original weight with deionized water. In drying, the color of the yeast darkens and it is assumed that some autolysis occurs; and the grinding facilitates rehydration and appears to have a destructive effect on cell walls. The rehydrated yeast is mixed with potassium chloride and incubated with stirring for eighteen hours at 4 degrees C. The mixture is then centrifuged and the supernatant liquid which is a solution of the CoA-SPC activity is recovered. This solution may be purified by further treatment, such as affinity chromatography; but I have found that, in practice, the crude solution is preferred.

The erythrocytes, red blood cells, for combination in one form of the composition are prepared by fixing the cells with formalin, glutaraldehyde or pyruvicaldehyde by conventional procedure, washing the cells in deionized water and resuspending the cells in phosphate buffer saline at pH 6.4.

The CoA-SPC solution in excess of the amount required to bond to substantially all of the cells is added to the suspension of cells and thoroughly mixed. Glutaraldehyde for binding the CoA-SPC to the cells is then added to give a final glutaraldehyde concentration of about 1.5%. After a further mixing for an additional two hours, the cell suspension was washed with phosphate buffer saline at pH 6.4 for storage as a stock suspension. Tannic acid 1:40,000 can also be used to bind CoA-SPC to the cells.

In an alternative form of the composition, CoA-SPC solution is added to a styrene polymer or copolymer latex, thoroughly mixed and incubated for eighteen hours at 37 degrees C. to bond the CoA-SPC physically or chemically firmly to the latex particles.

Latices providing suitable particles for use in the present composition include latices of polymers of styrene or copolymers of styrene with other monomers containing at least about 60% of styrene in the copolymer and having particle sizes of from about 0.05 to about 0.8 micron. A preferred latex is a carboxy modified butadiene-sytrene latex, such as that supplied by the Monsanto Chemical Company as 5450 and 5250.

Detection of tumor antigens by the method of the present invention may be effected by direct or indirect agglutination procedures. In the direct method, a measured quantity of patient's serum is diluted with normal saline solution, introduced into a clean glass test tube and mixed well. Positive and negative control sera are introduced into separate tubes and the tubes are placed in a conventional mirror rack.

After shaking the suspension of CoA-SPC bonded to etythrocytes to insure uniformity, one drop of the suspension is added to each tube and the tubes are shaken vigorously. At this time the liquids in the tubes are uniformly translucent.

The tubes are permitted to stand for two hours, at the end of which time, the positive control will remain uniformly translucent as viewed from the mirror and the negative control will show a dark ring at the bottom of the tube. The tube containing patient's serum will have a dark ring at its bottom if no tumor antigen is present or will drop in a mat-like form appearing to remain uniformly translucent, showing agglutination of the bonded CoA-SPC if tumor antigen is present in the patient's serum.

In the indirect agglutination method of the present invention, a measured quantity of patient's serum diluted with normal saline solution is deposited in a glass tube. One drop of unbonded CoA-SPC in solution is added to the tube and mixed thoroughly and thereafter one drop of the bonded CoA-SPC is added and mixed thoroughly. The tube is placed in a mirror rack and let stand for two hours. In this case, the unbonded CoA-SPC will unite with any tumor antigen present in the serum and block agglutinative association of the bonded CoA-SPC with such antigens. Accordingly, if there is no ring in the bottom of the tube, the test indicates that no tumor antigen is present in the serum, while the presence of the ring at the bottom of the tube is an indication that the serum contains tumor antigens.

In an alternative procedure, particularly useful when the CoA-SPC is bonded to colorless latex particles, a drop of the serum sample is deposited within one of three circles marked on a glass test plate, which may be black for better contrast, and one drop of each of the negative and positive control sera are deposited separately in the other two circles. One drop of the CoA-SPC latex particle reagent is deposited and mixed with each of the previously deposited three drops. The slide is rotated with a gentle rocking motion while observing the slide. Agglutination is usually apparent as the development of small clumps in the liquid of drops containing tumor antigen within twenty seconds to one minute. The agglutination showing presence of tumor antigen or non-agglutination showing its absence in the serum being tested is verified by comparison of its appearance with the positive and negative control sera.

The following examples are given to aid in understanding the invention, but it is to be understood that the invention is not limited to the particular materials, proportions and other details of the procedures.

EXAMPLE 1

Red blood cells from sheep were fixed with formalin by conventional procedures, washed four times with deionized water and suspended in a phosphate buffer saline solution to a content of 10% by volume at pH 6.4. CoA-SPC solution was added in amount of 2.4% by volume based on the volume of the blood cell suspension and mixed with a magnetic stirrer for ten minutes. Glutaraldehyde was added to the suspension in amount giving a final concentration of 1.5% by weight and mixing was continued for an additional two hours to bind the CoA-SPC to the cells. The suspension was washed with five volumes of phosphate buffer saline at pH 6.4 and stored as a 10% stock solution. A working suspension was made by diluting the stock suspension to a final cell concentration of 1.5% with phosphate buffer saline at pH 6.4.

Ten microliters of patient's serum was added to 3 ml. of normal saline solution (0.85%) and the composition was well stirred.

Two hundred microliters of the diluted serum and two hundred microliters each of positive and negative control sera were placed in 10×75 mm. glass tubes and the tubes were placed in a mirror rack. The working suspension was shaken well to insure uniformity and one drop of the solution was added to each tube and the tubes were shaken vigorously.

The tubes were allowed to stand in the rack for two hours and the results read. The negative control showed a dark ring in the bottom of the tube, the positive control showed no ring and the patient's sera showed no ring indicating the presence in that serum of tumor antigens.

EXAMPLE 2

In a modification of Example 1 to provide a semiquantitative test, eight tubes were placed in the mirror rack. Two hundred microliters of the patient's diluted serum were placed in the first tube and two hundred microliters of normal saline were added to each of the eight tubes. The sample in the first tube was mixed, two hundred microliters were withdrawn and transferred to the second tube and mixed. This was repeated through the eighth tube and after mixing in that tube two hundred microliters were withdrawn from that tube and discarded. One drop of the cell suspension containing bound CoA-SPC was added to each tube and the tubes shaken. The titer of the serum is equal to the dilution of the most dilute tube that shows no ring in the bottom of the tube.

EXAMPLE 3

Human red blood cells were washed and formalin treated by conventional procedure and washed four times with deionized water. The cells were then resuspended in phosphate buffer saline at pH 6.4 in concentration of 10% by volume. The cell suspension was reacted with CoA-SPC and glutaraldehyde, washed and diluted to form a working suspension as in Example 1.

The suspension was used to test patient's serum against positive and negative control sera as in Example 1 and similar results were obtained.

EXAMPLE 4

Human red blood cells were washed and formalin treated and then further washed with deionized water prior to resuspension in phosphate buffer saline at pH 6.4 to provide a cell concentration of 10% by volume.

Tumor antigen CoA-SPC binding protein was isolated by affinity chromatography and 10 ml. of this solution was added to the red blood cell suspension and allowed to mix for thirty minutes. Glutaraldehyde to the amount of 1.5% was added to the cell suspension and mixed with a magnetic stirrer for two hours. The suspension was then washed twice with five volumes of phosphate buffer saline at pH 6.4 and a working suspension was made by diluting the cell suspension with phosphate buffer saline at pH 6.4 to a final cell concentration of 1.5%.

Two hundred microliters of patient's serum diluted 1:300 with normal saline solution was introduced into a 10×75 mm. glass tube. One drop of diluted CoA-SPC was added to the tube mixed with the serum and thereafter one drop of the above prepared tumor antigen bonded red blood cells was added. The tube was placed in a mirror rack, shaken and let stand for two hours. In this case, the negative control has no ring in the bottom of the tube, the positive control has a ring at the bottom of the tube and the patient serum had a ring showing the presence of tumor antigen.

EXAMPLE 5

A reliability study was made using the procedure of Example 1 in which 180 samples of blood from blood banks of which all were considered negative and 180 samples drawn from patients with various carcinomas were tested.

Of the 180 samples considered negative, 179 were found to be negative and 1 was found positive by the procedure. Of the 180 samples considered positive, 177 were found positive by the procedure and 3 were found negative. The specificity was thus 0.6% false positive readings and 1.7% false negative readings.

EXAMPLE 6

2000 ml. of a 49% solids latex of a carboxyl modified styrene-butadiene copolymer having a particle size of 0.6 micron and pH of 8.2 was added to 24 ml. of crude CoA-SPC, and mixed for thirty minutes followed by incubation for eighteen hours at 37 degrees C. A working suspension was made by diluting the latex with 0.1 M glycine buffer to provide a final latex concentration of 1.2%. 0.1% of a preservative, Thimersol, was added as a preservative. A drop of patient's serum sample was deposited within one of three circle marked on a clean, dry black glass test plate and one drop each of the negative and positive control sera are deposited separately on the other two circles. One drop of the above prepared working suspension was dispensed on each of the three circles and mixed well individually with the sera in that circle using separate stirring sticks. The test plate was rotated with a gentle rocking motion while observing the circles for evidence of agglutination within twenty seconds to one minute.

Agglutination occurred in the patient's sera as evidenced by the development of small clumps in the liquid and the test was considered positive for the presence of tumor antigen. This agglutination was verified by comparison with the positive and negative control sera. If no difference in agglutination between the patient's serum and the negative control serum had been, the test would have been considered to be negative.

I claim:

1. A composition for direct or indirect agglutination testing of human serum for the presence or absence of tumor markers in the serum, comprising an aqueous suspension of CoA-SPC bonded to human or animal erythrocytes or to latex particles.

2. The composition as defined in claim 1 in which said erythrocytes and CoA-SPC are mixed in the ratio of from about 10% erythrocytes to about 2.4% CoA-SPC by volume and a unit of CoA-SPC is chemically bound to substantially every erythrocyte cell.

3. The composition as defined in claim 2 in which the aqueous phase of said suspension is a phosphate buffer saline and the pH is about 6.4.

4. The composition as defined in claim 3 in which said CoA-SPC and erythrocytes are bound by an aldehyde.

5. The composition as defined in claim 1 in which said latex particles are polymers of styrene or copolymers of styrene with other monomers containing at least about 60% of styrene in the copolymer and having particle sizes of from about 0.05 to about 0.8 micron.

6. The composition as defined in claim 5 in which said latex particles and CoA-SPC are combined in a ratio to provide a unit of CoA-SPC bound to substantially every latex particle.

7. The composition as defined in claim 6 in which said latex particles are a carboxyl modified copolymer of styrene and butadiene and said suspension is diluted to a latex concentration of 1.2% with 0.1 M glycine buffer.

8. A method for direct or indirect agglutination detection of tumor antigens in human serum, comprising mixing a measured quantity of a solution of the serum to be tested in normal saline solution with an aqueous suspension of CoA-SPC bonded to human or animal erythrocytes or to latex particles, and allowing the mixture to stand for reaction and agglutination of the erythrocytes- or particle- bonded CoA-SPC with any tumor antigen present in said serum.

9. The method as defined in claim 8 in which said combined CoA-SPC and erythrocytes are mixed in the ratio of about 10% erythrocytes to about 2.4% CoA-SPC by volume to bind a unit of CoA-SPC to substantially every erythrocyte cell, said aqueous suspension has an erythrocytes concentration of about 1.5% by volume and is buffered with phosphate buffer saline at a pH of about 6.4, and one drop of said suspension is added with mixing to 200 microliters of a solution of one part by volume of the serum in at least 100 parts by volume of normal saline solution.

10. The method as defined in claim 9 for direct agglutination detection of tumor antigens in human sera in which said serum solution is disposed in a transparent tube before addition of said drop of suspension and presence of tumor antigen in said serum is established if no dark ring forms on the bottom of said tube.

11. The method as defined in claim 9 for indirect agglutination detection of tumor antigens in which said serum solution is disposed in a transparent tube, one drop of an aqueous suspension CoA-SPC is added to the mixture of serum solution and suspension of CoA-SPC binding protein bonded to erythrocytes and presence of tumor antigens in said serum is established by formation of a dark ring on the bottom of said tube.

12. The method as defined in claim 10 in which semi-quantitation of tumor antigen is determined by disposing successively more dilute solutions of serum in successive tubes, the titer being equal to the dilution of the last tube which forms no dark ring on the bottom of that tube.

13. The method as defined in claim 8 in which said CoA-SPC is bonded physically or chemically to latex particles of polymers of styrene or copolymers of styrene with other monomers containing at least about 60% of styrene in the copolymer and having particle sizes of from about 0.05 to about 0.8 micron.

14. The method as defined in claim 9 in which said latex particles and CoA-SPC are mixed in a ratio to bind a unit of CoA-SPC to substantially every particle of said latex and said suspension has a latex solids concentration of about 1.2%.

* * * * *